(12) United States Patent
Schenk

(10) Patent No.: US 9,517,466 B2
(45) Date of Patent: Dec. 13, 2016

(54) MEASURING CASSETTE AND MEASURING DEVICE FOR THE DETECTION OF TARGET MOLECULES IN A LIQUID SAMPLE BY MEASUREMENT OF FLUORESCENCE EMISSION AFTER EXCITATION IN AN EVANESCENT FIELD

(75) Inventor: Roland Schenk, Kirchheim (DE)

(73) Assignee: DiaSys Diagnostic Systems GmbH, Holzheim (DE)

( * ) Notice: Subject to any disclaimer, the term of this patent is extended or adjusted under 35 U.S.C. 154(b) by 668 days.

(21) Appl. No.: 13/811,959

(22) PCT Filed: Jul. 19, 2011

(86) PCT No.: PCT/EP2011/062363
§ 371 (c)(1),
(2), (4) Date: Mar. 13, 2013

(87) PCT Pub. No.: WO2012/016824
PCT Pub. Date: Feb. 9, 2012

(65) Prior Publication Data
US 2013/0164857 A1   Jun. 27, 2013
US 2015/0079694 A2   Mar. 19, 2015

(30) Foreign Application Priority Data
Jul. 26, 2010   (DE) .................. 10 2010 038 431

(51) Int. Cl.
*G01N 21/00*   (2006.01)
*G01N 21/75*   (2006.01)
(Continued)

(52) U.S. Cl.
CPC ..................................... *B01L 3/508* (2013.01)

(58) Field of Classification Search
CPC ............ G01N 21/648; G01N 33/54373; G01N 21/7703; G01N 21/05; G01N 21/552; G01N 21/6428; G01N 2021/0346; G01N 21/553; G01N 21/6452; G01N 2021/058; G01N 15/1484; G01N 15/147; G01N 15/1434
See application file for complete search history.

(56) References Cited

U.S. PATENT DOCUMENTS 5,134,445 A * 7/1992 Toge .......................... 356/336
5,873,990 A * 2/1999 Wojciechowski et al. ... 204/406
(Continued)

FOREIGN PATENT DOCUMENTS

DE   196 28 002   12/1997
DE   197 11 281   4/1998
(Continued)

OTHER PUBLICATIONS

Sapsford et al., "Fluorescence-based array biosensors for detection of biohazards", J. Appl. Microbiol., 2004, v. 96, pp. 47-58.*
(Continued)

*Primary Examiner* — Yelena G Gakh
(74) *Attorney, Agent, or Firm* — Drinker Biddle & Reath LLP

(57) ABSTRACT

An interchangeable disposable measuring cassette for insertion into a measuring apparatus for detecting target molecules in a liquid sample by measuring fluorescence emission has a flow measurement cell in which an excitation radiation provided by the measuring apparatus produces an evanescent field in the liquid sample beyond a boundary layer for the liquid sample and the measurement cell. To be better able to ensure that no sample liquid can cross from the measurement cell into the measuring apparatus, the measuring cassette includes a body including an optically transparent material and a base in contact with the underside of the body. The measurement cell is formed by a cutout provided in the body, the base, or both. The areas on which the body (Continued)

Figure 1:
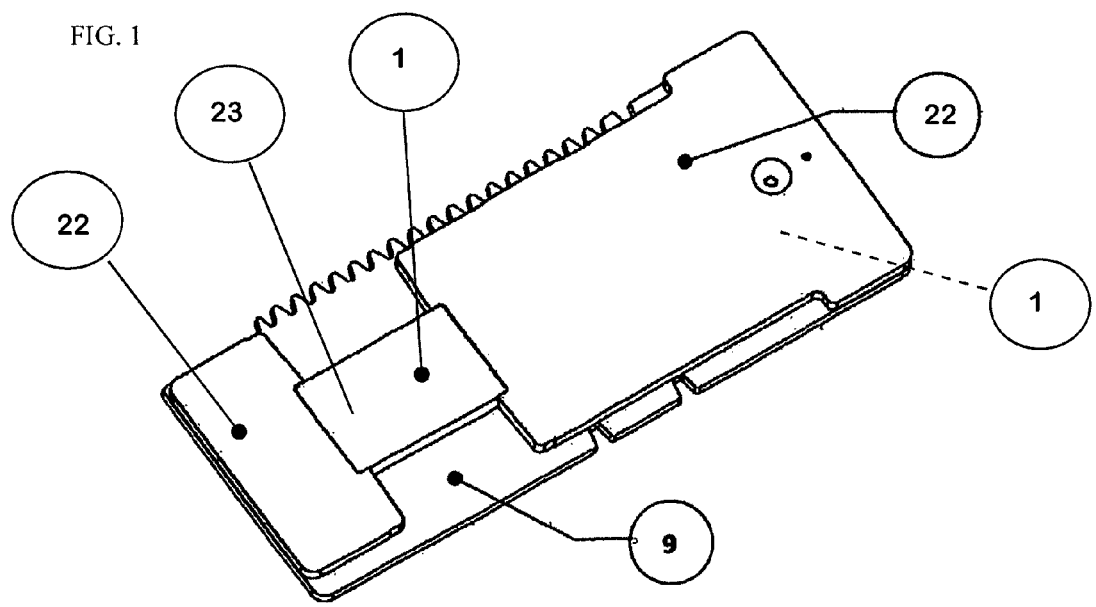

and the base are on top of one another around this cutout are connected to one another directly and in fluid-tight fashion by laser welding.

20 Claims, 4 Drawing Sheets
(1 of 4 Drawing Sheet(s) Filed in Color)

(51) Int. Cl.
*G01N 21/03* (2006.01)
*B01L 3/00* (2006.01)

(56) References Cited

U.S. PATENT DOCUMENTS

| | | | |
|---|---|---|---|
| 6,274,872 | B1 | 8/2001 | Katerkamp |
| 6,698,454 | B2 | 3/2004 | Sjölander et al. |
| 2002/0128593 | A1 | 9/2002 | Sjolander et al. |
| 2004/0189311 | A1* | 9/2004 | Glezer et al. ............ 324/444 |
| 2007/0010702 | A1 | 1/2007 | Wang et al. |
| 2009/0163377 | A1 | 6/2009 | Alexandre et al. |
| 2009/0197277 | A1 | 8/2009 | Beard et al. |
| 2010/0060998 | A1 | 3/2010 | Sekihara et al. |
| 2010/0220318 | A1 | 9/2010 | Moll et al. |

FOREIGN PATENT DOCUMENTS

| | | |
|---|---|---|
| DE | 601 30 679 | 7/2008 |
| EP | 0 774 657 | 5/1997 |
| EP | 1 347 284 | 9/2003 |
| EP | 1 635 161 | 3/2006 |
| JP | 2007-3464 | 1/2007 |
| WO | 2004/106901 | 12/2004 |
| WO | 2009/057024 | 5/2009 |

OTHER PUBLICATIONS

Axelrod, "Evanescent Excitation and Emission in Fluorescence Microscopy", Biophys. J., Apr. 2013, v. 104, pp. 1401-1409.*
Pawlak et al., "Zeptosens' protein microarrays: A novel high performance microarray platform for low abundance protein analysis" Proteomics, 2002, v. 2, pp. 383-393.*
Schmitt et al., "Evanescent field Sensors Based on Tantalum Pentoxide Waveguides—A Review", Sensors, 2008, v. 8, pp. 711-738.*
Grandin et al., "Waveguide excitation fluorescence microscopy: A new tool for sensing and imaging the biointerface", Biosensors and Bioelectronics, 2006, v. 2, pp. 1476-1482.*
Abed, Stéphane, "Soudage par faisceau laser, des perspectives industrielles", Plastiques & Elastomeres Magazine, Aug./Sep. 2002, pp. 20-23.
Chen, Jie-Wei et al., "Transmission laser welding of plastics for microsystem packaging", MicroEngineering 99, 1999, pp. 81-88, Mainz.
Klein, Heiner et al., "Laser Beam Welding of Plastic Micro Parts", ANTEC '99, May 2-6, 1999, pp. 1406-1410, vol. 1, New York City.
Neilley, Robert, "Lasers take aim at welding plastics", Injection Molding, Apr. 1999, pp. 103-106.
Paige, Jacqueline D., "Lasers Bond Difficult Plastics", Photonics Spectra, Apr. 1999, pp. 30 and 33.
Pfleging, W. et al., "Laser Patterning and Welding of Transparent Polymers for Microfluidic Device Fabrication", Proc. of SPIE, 2006, pp. 610705-1-610705-12, vol. 6107.
Schelb, Mauno et al., "Fluorescence excitation on monolithically integrated all-polymer chips", Journal of Biomedical Optics, Jul./Aug. 2010, pp. 041517-1-041517-5, vol. 15(4).
Wiemer, Karin, "Laserschweißen ohne Grenzen", Kunststoffe, 2004, pp. 48-51, vol. 4.

* cited by examiner

MEASURING CASSETTE AND MEASURING DEVICE FOR THE DETECTION OF TARGET MOLECULES IN A LIQUID SAMPLE BY MEASUREMENT OF FLUORESCENCE EMISSION AFTER EXCITATION IN AN EVANESCENT FIELD

CROSS REFERENCE TO RELATED APPLICATIONS

This application is a National Stage of International Application No. PCT/EP2011/062363 filed Jul. 19, 2011, which claims benefit of German Patent Application No. 10 2010 038 431.3 filed Jul. 26, 2010, both of which are herein incorporated by reference in their entirety.

The present invention relates to a replaceable disposable measuring cassette for introduction into a measuring device for detecting target molecules in a liquid sample by measurement of fluorescence emission, wherein the measuring cassette has a flow-through measuring cell in which excitation radiation provided by the measuring device generates an evanescent field in the liquid sample on the other side of a boundary surface of the liquid sample and measuring cell. The present invention moreover relates to a process for the production of such a measuring cassette, and a measuring device for the detection of target molecules in a liquid sample by measurement of fluorescence emission after excitation in an evanescent field, wherein the measuring device has an insertion shaft for the abovementioned measuring cassette. The present invention furthermore relates to a method for detecting target molecules in a liquid sample by measurement of fluorescence emission after excitation in the evanescent field, in which the abovementioned measuring cassette or the abovementioned measuring device is employed.

With a measuring cassette or measuring device of the abovementioned type, target molecules in a liquid sample can be recorded qualitatively or quantitatively by measurement of fluorescence emission after excitation in the evanescent field. The target molecules mentioned either can emit fluorescent radiation themselves by evanescent field excitation or—if they are not capable of this—can be rendered appropriately detectable by coupling with a fluorescent marker.

In fluorescence excitation in the evanescent field, light of a suitable wavelength (excitation radiation) is directed on to a boundary surface between the liquid sample to be analysed and a surface of an optically transparent material, so that the excitation radiation is reflected totally with simultaneous generation of an evanescent field in the liquid sample. The evanescent field interacts with the liquid sample, and can excite fluorophores present in this field to fluorescence radiation. This fluorescence can be recorded with a detector.

A measuring device with which this type of measurement can be carried out is already known from the prior art. DE 196 28 002 and DE 197 11 281 describe a device for carrying out fluorescence immunotests by means of evanescent field excitation, in which a light beam is directed at an angle suitable for total reflection on to a boundary surface of a receiving region constructed in the form of a cuvette, wherein the receiving region is arranged between an optically transparent base plate and a cover plate. The receiving region here preferably has a thickness of between 0.001 and 0.5 mm and is defined by a spacer arranged between the base plate and the cover plate. In this context, the spacer is preferably a thin foil provided with an adhesive film on both sides, or a thin adhesive film which can be stuck on the one hand on the base plate and on the other hand on the cover plate.

In the devices from the prior art which are described above, the excitation radiation is effected through the transparent base plate, and the fluorescence emission emerges likewise through the transparent base plate in the downwards direction. The detector and the excitation source for recording the fluorescence emission are accordingly arranged underneath the measuring cell formed by the base plate, spacer and cover plate.

A disadvantage of the system from the prior art with adhesive foil or adhesive film is that adhesive foil and adhesive film have only a limited storage stability, so that during a long storage period changes in the material may occur, which under certain circumstances can even lead to non-fluid-tight areas arising on the measuring cassette, for example due to small cracks in the adhesive foil or the adhesive film. If such non-fluid-tight areas arise, liquid sample may possibly leak from the measuring cell arrangement and enter into the measuring device. In the case of the devices from the prior art which are described above, the sample here could, for example, drip on to the fluorescence emission detector arranged underneath the measuring cell or the excitation source likewise arranged in this region, which can lead to an impairment in the fluorescence detection and therefore to an impairment in all further measurements.

Such a device with an adhesive film furthermore can be produced only with great manual effort, since the application of the adhesive film can be automated only with difficulty.

The adhesive film moreover is conventionally made of a flexible material, which under certain circumstances relaxes in the course of time, as a result of which the height of the measuring cell may change. The systems known from the prior art with adhesive foil or adhesive film therefore also have the disadvantage that the height of the measuring cell can vary over time and in dependence on the amount of the pressure bearing on the base plate and the cover, which may be associated with undesirable measurement inaccuracies.

There was therefore a need for an improvement in the devices known from the prior art for detecting target molecules in a liquid sample by measurement of fluorescence emission, in order to ensure that no sample liquid can arrive at the fluorescence detector from the region in the measuring cell where the liquid sample is excited to fluorescence emission.

The object of the present invention is therefore to provide a device for detecting target molecules in a liquid sample by measurement of fluorescence emission, in which it is ensured to a better degree that no sample liquid from the measuring cell can enter into the measuring device, in particular cannot arrive at the fluorescence detector or at the excitation source.

This object is achieved according to the invention by providing a measuring cassette of the abovementioned type, wherein the measuring cassette comprises a body of an optically transparent material and a base lying adjacent to the under-side of the body, wherein the measuring cell is formed by a recess which is provided in the body, in the base or both in the body and in the base, wherein the areas on which the body and the base lie on one another around this recess are bonded to one another directly and in a fluid-tight manner by laser welding.

In contrast to the measuring cell of the devices known from the prior art, the measuring cell of the measuring cassette according to the invention is constructed such that the optically transparent region is provided on the upper side thereof by the optically transparent material of the body. The fluorescence excitation and fluorescence measurement accordingly are effected from above through the optically transparent material of the body. The fluorescence detector can accordingly be arranged above the measuring cell region, which avoids sample liquid leaking from the region of the measuring cell arriving at the fluorescence detector. Moreover, if the optical components are arranged underneath the measuring cell, they are more easily contaminated by dust. If an optical system operating from above is used, the danger of contamination of the optical components with dust is significantly lower.

In order additionally to ensure that no sample liquid from the region of the measuring cell can enter into the measuring device, the present invention moreover provides for the parts of the measuring cassette which form the measuring cell to be joined to one another directly and in a fluid-tight manner by laser welding. Somewhat more precisely, the present invention provides that the measuring cassette comprises, for the purpose of formation of a measuring cell, a body of an optically transparent material and a base lying adjacent to the under-side of the body. In this context, the measuring cell is formed either by a recess provided in the transparent material of the body or by a recess provided in the base. In this context, the recess is covered by the other particular component (base or body). Alternatively, the recess can also be provided both in the body and in the base, wherein the recessed region on the one side (e.g. in the body) and the recessed region on the other side (e.g. in the base) together define the recess which forms the area of the measuring cell.

In each case, the areas of the body and of the base present lying adjacent to one another around the recess are bonded to one another directly and in a fluid-tight manner by laser welding. Bonding by laser welding has the advantage over gluing of the measuring cell components—as is provided in the abovementioned prior art—that by this means a direct bond is generated between the components, without a layer of another material being present between the components.

The bonding according to the invention by laser welding ensures absolutely that the measuring cell is sealed with respect to the liquid present in the measuring cell. In this context the absolute seal is also ensured if the liquid in the measuring cell is under pressure, e.g. if the sample liquid is moved through the measuring cell with pressure. For example, the measuring cassette according to the invention ensures absolute fluid-tightness even under a pressure of up to 300 mbar. This also applies conversely to a negative pressure situation in the measuring cell. For example, if a reduced pressure of down to −300 mbar is generated in the measuring cell, it is ensured that due to the measuring cassette being closed in a fluid-tight manner, no air can enter into the measuring cell from the outside.

Bonding by laser welding moreover has a significantly higher long-term stability than the bonding via an adhesive foil or an adhesive film known from the prior art.

Bonding of the components defining the measuring cell by laser welding moreover is also of advantage from the production point of view, since only two components are processed, without a foil or a layer of adhesive in the required shape also having to be arranged or applied between these components. It is therefore possible for the production of the measuring cassette according to the invention to be automated to a better degree.

This configuration moreover is more user-friendly, since by this means cleaning steps which are required in the case of the corresponding devices from the prior art are omitted, since once the adhesive film in the known devices has become non-fluid-tight, all the optical components lying underneath the measuring cell must be cleaned.

The term "optically transparent" is used here such that an optically transparent material is transparent both to the excitation radiation and to the fluorescence emission. Preferably, the transparent material of the body is glass or an optically transparent plastic. In the case of plastics, these can be selected, for example, from polycarbonates (PC), poly (methyl methacrylates) (PMMA, Rohaglas) and polyolefins (Topas, COC). Preferably, in the case of plastic this is a plastic suitable for laser welding, wherein optically transparent plastics which are suitable for laser welding are known to the person skilled in the art.

The material from which the base is made is preferably a plastic. The plastic is particularly preferably a poly(methyl methacrylate) (PMMA) or a polyolefin.

If the material of the body is glass or a plastic which is not suitable for laser welding, the material of the base must be made of a plastic which is suitable for laser welding. On the other hand, if the base is made of a material which is not suitable for laser welding, the material of the body must be a plastics material which is suitable for laser welding. Particularly preferably, the body material and the base material are the same plastics material which is suitable for laser welding.

Advantageously, the body and base are each one-component parts, which are preferably produced in the injection moulding process. This has the advantage that these components have no seams or transition points between different materials through which possibly sample liquid could leak or air could be drawn in—particularly if a positive or negative pressure is built up in the system.

Trapping molecules which capture the molecules of interest from the sample liquid and fix them on the boundary surface so that the fluorescence can be excited and measured there are preferably arranged in the optical region at the boundary surface between the optically transparent material of the body and the sample liquid. Various receptor-ligand systems can be employed for this. These systems include, inter alia, antibody-antigen, lectin-carbohydrate, DNA- or RNA-complementary nucleic acid, DNA- or RNA-protein, hormone-receptor, enzyme-enzyme cofactors, protein G- or protein A-immunoglobulin or avidin-biotin. Preferably, the trapping molecules are printed on to the boundary surface by means of a printing process, e.g. by means of a piezo dispensing system.

In one embodiment of the present invention, the measuring cassette has a sample channel which is in fluid contact with the measuring cell and on which is provided at least one of the following arrangements a) to c):

a) a zone for dissolving a tracer,
b) a sample mixing region and/or
c) a liquid detection region, wherein the sample channel and the arrangements a), b) and/or c) provided thereon are formed by a recess which is provided in the body, in the base or both in the body and in the base, wherein the areas on which the body and the base lie on one another around this recess are bonded to one another directly and in a fluid-tight manner by laser welding.

Preferably, the height of the sample channel is not more than 300 µm. Particularly preferably, the height of the channel is in the range of from 100 to 300 µm.

Preferably, one or more liquid detection regions (fluidic sensor) are provided on the sample channel. Such a liquid detection region on the sample channel serves to detect undesirable air bubbles in the sample channel or to establish whether sample liquid is present at a particular point of the sample channel by establishing the transition between air and sample in the sample channel.

In a preferred embodiment of the invention, the liquid detection is effected by an optical method in which a light beam is passed through the sample channel in order to establish with the aid of the refraction of the light beam whether air or sample liquid is present in the sample channel at this point. In this respect, it is expedient and advantageous to embed at least sections of the sample channel into an optically transparent material, so that a light beam can be passed through the sample channel for the purpose of fluid detection. Preferably, the section of the sample channel in which a liquid detection is to be carried out is present in the transparent material of the body. If, in such an embodiment of the invention, the base is made of a material which is not transparent to the light beam, recesses through which the light beam can enter or emerge before entry into the sample channel or after transillumination of the sample channel are expediently present in the region of the beam path of the light beam for detection of liquid in the base of the measuring cassette.

The liquid detection region can also be used for determination of the sample volume employed, e.g. via the parameters of time and pump speed or the position of the sensors relative to one another.

In cases where the molecules of interest (target molecules) in the sample cannot themselves be excited to fluorescence emission, these are marked with suitable fluorescence markers (tracers). In a preferred embodiment of the present invention, at least one zone for dissolving a tracer and optionally at least one sample mixing region are provided for this on the sample channel provided in the body for the purpose of reaction/conversion with the sample in the measuring cassette. In this zone further reagents, e.g. reagent to adjust the pH of the sample, lysis buffer or reagents for reducing non-specific binding, can also be dissolved, and likewise mixed with the sample in the mixing region.

In one embodiment of the present invention, the body of the measuring cassette is produced as a one-component part in the injection moulding process. In another embodiment, the base is produced as a one-component part in the injection moulding process. In yet a further embodiment, both the body and the base are each produced as one-component parts in the injection moulding process.

The fluorescence-marked tracers are preferably printed on by means of a printing process, e.g. by means of a piezo dispensing system, into the zone provided for dissolving thereof.

The sample mixing region is preferably a so-called snake mixer in which an efficient thorough mixing of the sample can be achieved through the serpentine-like arrangement of the sample channel.

When a measuring cassette according to the invention is introduced into a suitable measuring device, minimal deviations from the ideal position may easily occur. Even though these deviations are only minimal, this can have significant effects on the precise optical measurement method. In a preferred embodiment of the invention, at the point where the excitation radiation enters into the body the body therefore forms a converging lens with which the beam of the excitation radiation is always directed reliably to the desired point of the boundary surface of the liquid sample and the surface of the transparent material of the body. This converging lens integrated into the body can compensate for the insertion variations described above. In particular, compared with systems known from the prior art, by this means positioning-related variations of the evanescent field (penetration depth, intensity) can be reduced significantly in that the alignment of the excitation radiation by the converging lens is always effected exactly at the region in which the fluorescence emission which arises there is to be measured, i.e. within the predetermined limits of the region.

Preferably, the excitation radiation is aligned by the converging lens on the region in which the fluorescence emission to be measured is to be generated, i.e. centrally along the longitudinal axis of the measuring cell. Preferably, the area of the excitation region is circular or elliptical.

Particularly preferably, the area of the excitation region is elliptical having dimensions in the region of about 0.7×0.25 mm.

The measurement cassette has a sample filling opening for filling the measuring cassette with the liquid sample. Preferably, the sample filling opening is provided on the upper side of the body of the measuring cassette. In one embodiment of the invention, the sample filling opening can be closed in a pressure-tight manner. Preferably, the sample filling opening can be closed and be pressure-tight up to a pressure or reduced pressure of +/−100 mbar. Preferably, pressure seals, which particularly preferably are made of polypropylene, are provided for this. In a particularly preferred embodiment, the closure for closing the sample filling opening is a slide valve which can be pushed from an opened position into a closed position after filling of the sample, wherein the slide valve is pressed on to a pressure seal provided on the sample filling opening due to the geometry of the slide guide.

In order to be able to generate a positive or negative pressure in a sample channel of a measuring cassette according to the invention, in preferred embodiments of the invention at least one pressure opening is provided which can be connected to a pressure source and is in ("pressure") contact with the sample channel. Positive or negative pressure can be built up in the sample channel in this manner, by means of which the sample can be moved through the sample channel. Preferably, the pressure openings are configured such that a pressure of at least +/−100 mbar can be applied. In these embodiments, the sample channel is also expediently configured such that it withstands this pressure without problems.

In a particular embodiment, a sample waste region in which sample liquid which has already been analysed can be accommodated is provided in the measuring cassette at the end of the sample channel. This has the advantage that the sample liquid which has already been analysed does not leave the measuring cassette after flowing through the measuring cell, but remains in the measuring cassette. The sample waste region can be provided either in the body or in the base of the measuring cassette.

In one embodiment of the present invention, in addition to the body and the base, a cover which at least partly covers the body is provided on the measuring cassette, wherein recesses are provided at least in the region of the beam path of the excitation radiation and the fluorescence emission, so that the body is not covered by the cover in this region. The cover is firmly connected to the unit of the body and base. Preferably, the connection of the cover to the body and base is effected by hot caulking which extends through the cover, body and base. In the embodiments with the cover which have in their sample channel a liquid detection region for optical detection of liquid, a recess in the cover is provided in the region of the beam path of a light beam for detection of liquid, so that the optical detection of liquid is possible in spite of the cover.

For each measuring cassette batch, it is necessary also to supply batch-specific calibration data. In known systems, this is effected by a storage medium, such as e.g. a barcode or a memory chip (EEPROM). Ideally, such a medium is to be present on every measuring cassette, so that all the information for identification of a measuring cassette and in particular the associated batch calibration data are applied directly to this in the production process and can be recorded and verified by the measuring instrument when measuring with such a measuring cassette. In principle, however, the batch calibration data can always be determined only after the production of a batch has been concluded completely (i.e. including packaging). The period of time between the production of the first parts of a batch and the determination of said calibration data can be several hours to days. To maintain the stability of the reagents in such a measuring cassette, this requires that this is packed air- and light-tight. In order to apply said medium with the calibration data to the measuring cassette, an additional, cost- and time-intensive unpacking and packing step is therefore necessary, during which damage to the measuring cassette may additionally occur. In the case of many known systems, attempts are made to avoid this step by enclosing one of these media separately in a pack unit. The user must then either insert a memory chip with said information or read a barcode into the apparatus before the first use.

In order to bypass this cumbersome and not necessarily error-free process, a preferred embodiment of the measuring cassette according to the invention is provided with an electronic memory chip which can be written to and overwritten through the packaging even after packing of the measuring cassette. Preferably, this electronic memory chip is an RFID label. The RFID label can be provided either with or without additionally visually readable information.

The electronic memory chip can be applied to each measuring cassette continuously during the production process of a batch. Each measuring cassette therefore receives an individual, electronic number. Each measuring cassette can be packed in the desired packaging, for example a suitable primary packaging, directly after assembly thereof and stored under the required storage conditions. The application of the subsequently determined batch-specific information, e.g. the calibration data, can then be carried out in a contact-free manner through the packaging at any time, even e.g. in a refrigerated environment. A further advantage of this process is that in the context of regular production monitoring over the life cycle of a batch, a necessary recalibration can be carried out even after several months without impairment of the product integrity.

According to a further aspect of the present invention, a process for the production of a measuring cassette of the type described above is provided, wherein in this process the body and the base are produced as one-component parts in the injection moulding process. Both the body and the base are therefore in each case a one-piece component which can be produced from one material each. In the measuring cassette embodiments which also have a cover in addition to the body and base, the cover is also preferably produced as a one-component part in the injection moulding process. In the embodiments in which the measuring cassette has a closure for closing the sample filling opening, this closure is preferably an integral constituent of the one-component part on which the closure is provided.

In a preferred process, in the production of a measuring cassette with a cover connecting of the cover to the unit of the body and base is carried out by hot caulking. For this, the cover has appropriate pins of plastic which are passed through bores at the corresponding points in the body and base, and a positive-locking connection of the cover to the body is established at the base by thermoforming.

A further aspect of the present invention relates to a measuring device for the detection of target molecules in a liquid sample by measurement of fluorescence emission after excitation in an evanescent field, wherein the measuring device has an insertion shaft for a corresponding measuring cassette. In the insertion shaft of the measuring device, the measuring cassette is arranged in at least one position such that the light source for the excitation radiation arranged in the measuring device can provide an excitation radiation which meets the boundary surface of the liquid sample and measuring cell such that total reflection of the excitation radiation to form an evanescent field in the liquid sample is effected. The penetration depth and the intensity of the evanescent field can be influenced via the choice of the angle of the incident excitation beam. Preferably, the angle with which the excitation radiation meets the boundary surface is about 8 degrees.

A measuring device of the abovementioned type which has an insertion shaft for a measuring cassette according to the present invention is claimed in particular. Inter alia, the complete system of a measuring device of the abovementioned type and one or more measuring cassettes according to the present invention is also claimed. A measuring device of the abovementioned type with a measuring cassette according to the present invention inserted into the insertion shaft is claimed in particular.

In a preferred embodiment of the measuring device according to the invention, this also comprises arrangements with which a relative movement of the measuring cassette with respect to the light source for the excitation radiation can be performed, in order thus to bring various measuring cell regions into the beam path of the excitation radiation. In this manner, several different trapping zones can be provided in the measuring cell, in order to respond to several different analytes at the various trapping zones using only one light source.

In one alternative to the abovementioned embodiment, the measuring cell in the insertion shaft is moved optionally continuously or in a stepwise manner along an axis of movement from a first position into at least a second position, in order to bring various measuring cell regions into the beam path of the excitation radiation. As an alternative to this, the measuring device according to the invention can also be configured such that the light source for the excitation radiation can be moved continuously or in a stepwise manner along an axis of movement such that it aligns its excitation beam to various regions of the measuring cell.

Regardless of the alternative chosen, the light source for the excitation radiation is preferably provided in the measuring device such that the beam of the excitation radiation meets the measuring cell at an angle of 90 degrees to the direction of movement of the relative movement of the measuring cassette with respect to the light source. Inter alia, the path of the excitation beam through the body is minimized in this manner. Furthermore, always only a small section of the optically transparent material is illuminated. The path of the excitation beam through the body furthermore is always the same over the entire region travelled through by the excitation beam. Moreover, a better local resolution of the excitation light within the measuring cell is achieved overall. This advantage of the measuring device according to the invention means that a better signal to noise ratio is achieved.

In one embodiment of the measuring device according to the invention, this is distinguished in that it has a pressure source which, in the case of a measuring cassette which is inserted into the insertion shaft and has a pressure opening on the sample channel, is connected to the pressure openings of the sample channel such that a sample present in the sample channel can be moved through the sample channel by means of positive or negative pressure generated by the pressure source. Preferably, the pressure source and the connections of the pressure source to the pressure openings are configured such that a pressure of at least +/−100 mbar can be applied.

In a further aspect of the present invention, a method for detecting target molecules in a liquid sample by measurement of fluorescence emission after excitation in an evanescent field is described, wherein a measuring cassette according to the invention in combination with a measuring device according to the invention are employed in the method. All methods of the abovementioned type in which aqueous samples are analysed in a corresponding manner, for example also corresponding methods in environmental and foodstuffs analysis, are possible here. The method according to the invention is preferably immunoassays or DNA binding assays. However, the present invention is in no way limited to these, but includes all methods which can be realized in this connection in which target molecules are recorded qualitatively and/or quantitatively in a liquid sample by measurement of fluorescence emission after excitation in an evanescent field.

In one embodiment of the method according to the invention, the sample upon which the measurement is carried out is a treated or untreated aqueous sample for foodstuffs or environmental analysis. In connection with the present invention, a treated sample is to be understood as meaning a sample which has been taken from a sample source and has been treated by measures known to the person skilled in the art for the purpose of carrying out the measurement in order to facilitate or to improve the measurement procedure. One possibility for treatment of a sample is, for example, prior removal from the sample of components which possibly interfere in the measurement.

In an alternative embodiment of the method according to the invention, the sample upon which the measurement is carried out is a treated or untreated body fluid. The body fluid here can be selected, for example, from blood, urine, saliva etc. Treated body fluids can be, for example, blood plasma and serum. In the embodiments of the method according to the invention in which the sample is whole blood, the circumstance that under laminar flow in the measuring cell centralization of the blood corpuscles takes place is utilized, so that the evanescent field excitation can be effected in a region of the whole blood in which no impairment of the excitation or radiation emission by blood corpuscles is effected.

For the purpose of the original disclosure, it is pointed out that all the features such as are revealed to a person skilled in the art from the present description, the drawings and the claims, including if they have been described specifically only in connection with certain further features or represented in the subsequent figures, both individually and in any desired combinations, can be combined with other features or feature groups disclosed by the description or representation, as long as this has not been expressly ruled out or technical circumstances make such combinations impossible or senseless. Comprehensive, explicit explanation or representation of all conceivable combinations of features is dispensed with here merely for brevity and readability of the description.

Further individual features and combinations of features of the invention and further advantages of individual features and combinations of features of the invention emerge from the figures attached to this application and the following description thereof. It is pointed out in this connection that it goes without saying for the person skilled in the art that the embodiments represented in the figures merely serve to indicate by way of example features and combinations of features on the basis of possible embodiments of the present invention. The person skilled in the art will readily understand that beyond the embodiments represented in the figures, all other embodiments which have the features or combinations of features according to the invention mentioned in the claims and the description lie within the scope of protection of the invention. Comprehensive, explicit explanation or representation of all conceivable embodiments is dispensed with here merely for brevity and readability of the description.

The attached figures show in detail:

The patent or application file contains at least one drawing executed in color. Copies of this patent or patent application publication with color drawing(s) will be provided by the Office upon request and payment of the necessary fees.

Figure 2:
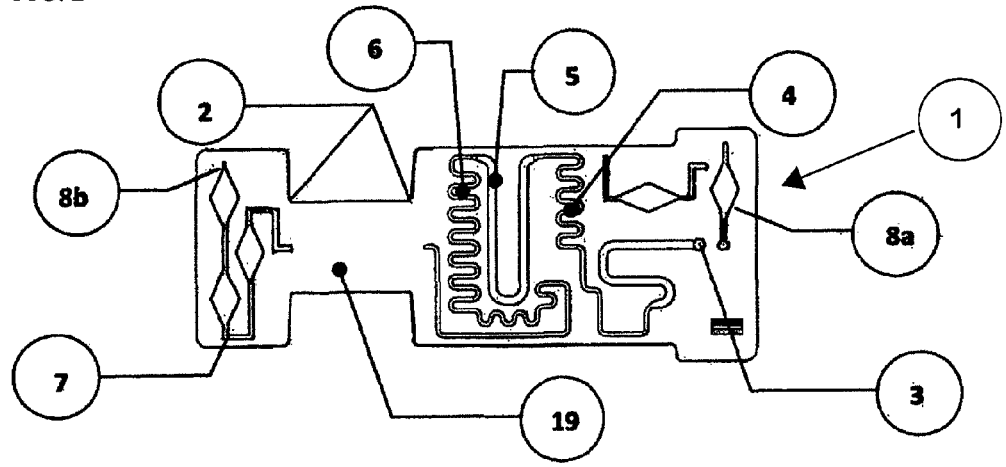
Figure 3:
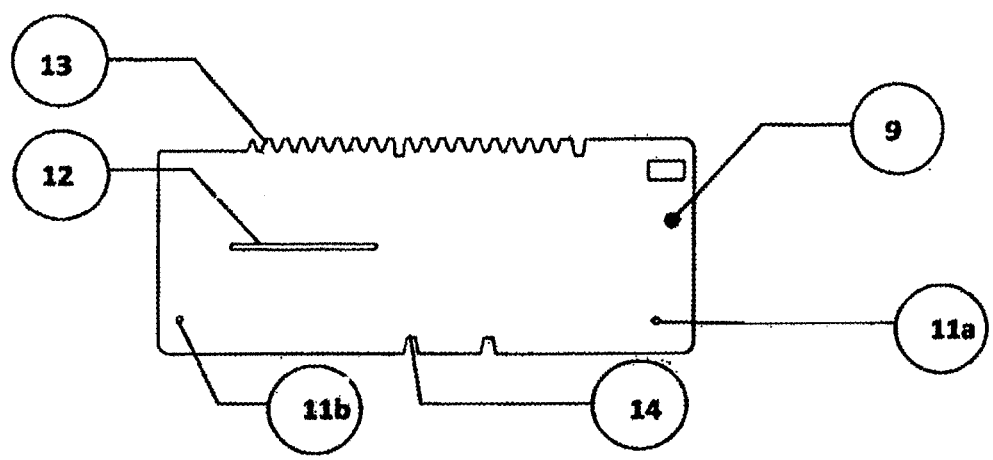
Figure 4:
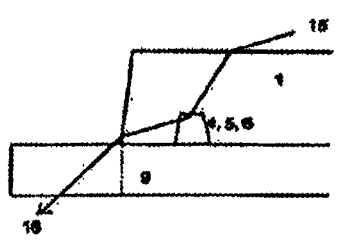
Figure 4:
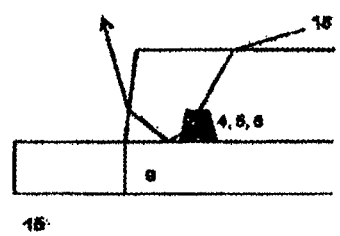
Figure 5:
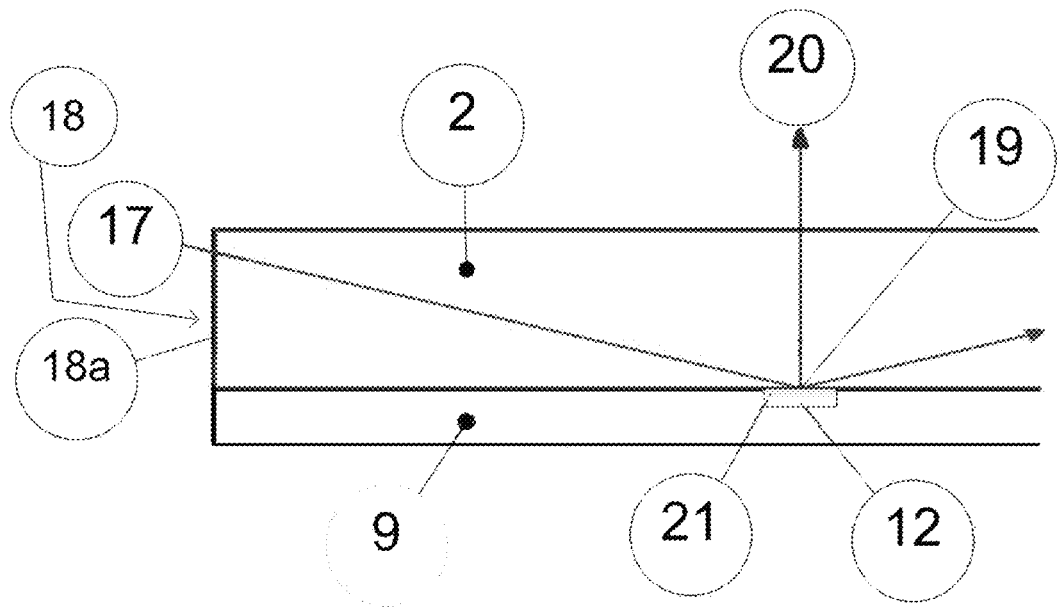
Figure 6:
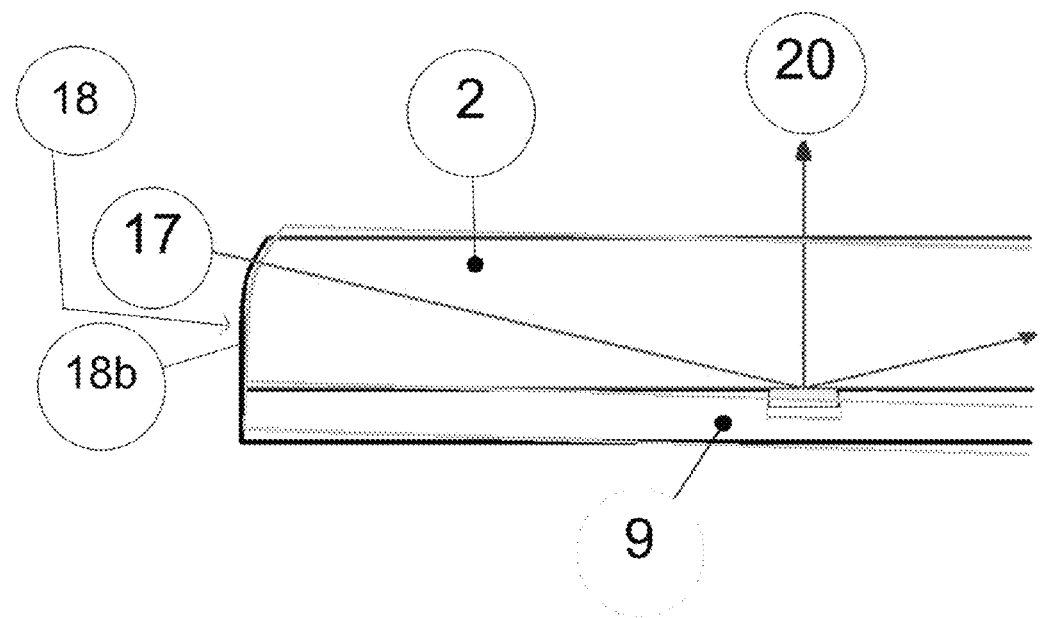
Figure 7:
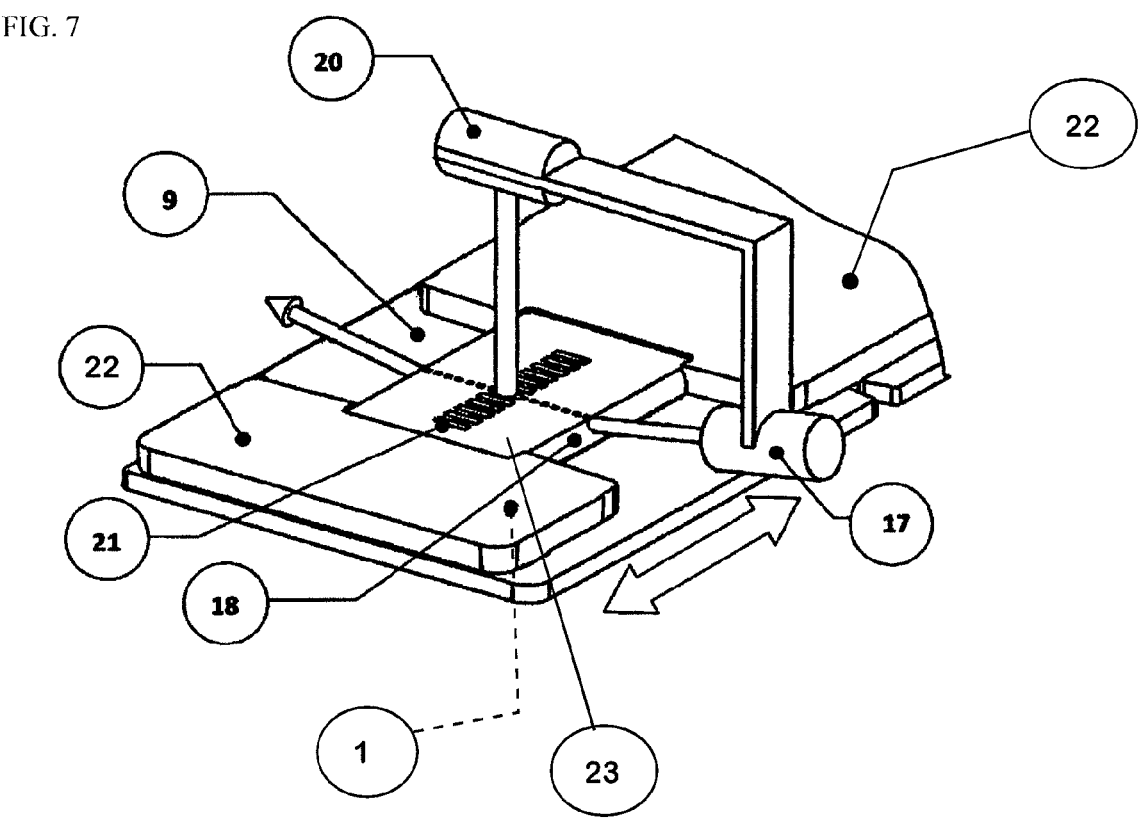

FIG. 1: plan view of an embodiment of a measuring cassette according to the invention, comprising a transparent body and a base, FIG. 2: plan view from underneath of the base-facing side of the body of an embodiment of a measuring cassette according to the invention (without showing the base lying on top), FIG. 3: plan view from the top of the base-facing side of the body of an embodiment of a measuring cassette according to the invention (without showing the body lying on top), FIG. 4: diagram of the principles of a fluidic sensor in an embodiment of a measuring cassette according to the invention in the case of a sample channel filled with air (a) and in the case of a sample channel filled with sample liquid (b), FIG. 5: diagram of a section through the region of an embodiment of a measuring cassette according to the invention in which the measuring cell is arranged, FIG. 6: diagram of a section through the region of an alternative embodiment of a measuring cassette according to the invention in which the measuring cell is arranged, wherein a converging lens for the excitation radiation is provided in the region, and FIG. 7: diagram of an embodiment of a measuring device according to the invention.

FIG. 1 shows a plan view of a measuring cassette according to the invention, comprising a transparent body (1) and a base (9) which are bonded to one another by a laser welding process. The body (1) and base (9) are produced as one-component parts in the injection moulding process. The cassette also includes a cover (22) connected to at least a portion of body (1) with a recess (23) in the cover that renders the body (1) not covered in that region.

FIG. 2 shows a plan view from underneath of the base-facing side of the body of a measuring cassette according to the invention (without showing the base lying on the body on this side). The body part comprises a sample filling opening (3) for filling with sample, connected directly and without branches to a microchannel structure (sample channel), having a mixing region (4), a zone for dissolving the tracer (5) and a further mixing region (6), an optical region (2) and a subsequent sample waste region (7). The channel ends (8a) and (8b) are configured such that these are connected to the base (9) at the pressure connection openings (11a) and (11b) present there.

In the plan view from the top of the base-facing side of the body of a measuring cassette according to the invention of FIG. 3 (without showing the body lying on top), the pressure connection openings (11a) and (11b) which are present in the base (9) and are mentioned in the description of FIG. 2 are to be seen.

In this context, the corresponding measuring device is to be configured such that the measuring cassette can be drawn in completely automatically with the aid of a toothed structure (13) and after conclusion of a measuring operation is ejected again completely automatically. The drawing in moreover is configured such that user errors during insertion of the measuring cassette into the corresponding measuring device are ruled out.

The embodiment of the measuring cassette according to the invention shown in FIGS. 2 and 3 is configured such that the filled-in sample can be moved by a positive or negative pressure between the sample and pressure connection openings (11a) or (11b) from the sample filling opening (3) through the fluid microchannels (4-6) and through the measuring cell (12). To generate the required pressure, the embodiment of the measuring device according to the invention into which the measuring cassette for carrying out the analysis is introduced expediently has a pressure source, such as e.g. a syringe, and connection possibilities on the pressure connection opening (11a) or (11b) of the measuring cassette, wherein the connection between the pressure source and pressure connection openings preferably is configured such that a pressure of at least ±100 mbar can be used. If positive/negative pressure is used via port 11a, the sample inlet must be closed. If port 11b is used, on the other hand, closure of the sample inlet is not necessary.

In the embodiment shown here, the microchannels (4-6) in the body part (1) are characterized in that there are no junctions at which air bubbles can be trapped, and the maximum difference in cross-section between the smallest and largest channel cross-section is a factor of 2, so that membrane formation and therefore a disturbance in the fluidics cannot occur.

During production of the measuring cassette, fluorescence-marked tracers are printed into the microchannel region (5) between the mixing regions (4, 6) by means of a printing process, e.g. a piezo dispensing system. Trapping molecules (21) are printed on to the boundary surface (19) of the optical element (2) within the region of the measuring cell (12) by means of the same process.

FIG. 4 illustrates the principle of a fluidic sensor for fluid detection in one embodiment of the measuring cassette according to the invention. In this context, fluid detection is effected by coupling light (15), e.g. by means of an LED, wherein it can be seen from the refraction of the coupled light beam whether or not sample liquid is present in this channel region. If the channel is empty, in this embodiment the difference in the refractive index between the body and air is selected such that the incident beam is refracted only to the extent that it meets a detector (16) lying opposite, e.g. a photodiode, whereas the difference in refractive index when the channel is filled means that the incident beam is refracted such that it is reflected at the body-base boundary surface and does not reach the detector (16) lying opposite. So that the light beam can reach said detector in the case of an empty channel, recesses (14) are provided in the base (9) at the appropriate points.

FIG. 5 shows a diagram of a section through the region of an embodiment of a measuring cassette according to the invention in which the measuring cell is arranged.

The measuring cell (12) can be filled with the sample to be analysed via a microchannel structure, such as is shown, for example, in FIGS. 2 and 3. The measuring cell (12) has an optically transparent region (2) which is a constituent of the body (1) lying on the base (9). This optically transparent region (2) has a light entry area (18) and a boundary surface of total reflection (19). The material of the optically transparent region (2) expediently has a higher refractive index than the samples to be measured.

When light (preferably monochromatic light) from a light source (17) in a measuring device in which the measuring cassette of FIG. 5 is arranged enters as a beam having a particular geometry (preferably elliptical or circular) via the light entry area (18) into the optically transparent region (2) at a suitable angle, the light beam meeting the boundary surface (19) undergoes total reflection.

As a result of the total reflection generated at the boundary surface (19), an evanescent field arises on the reverse thereof. The penetration depth and the intensity of said evanescent field can be influenced via the choice of the angle of the incident light beam.

In the embodiment shown here, a recess is provided in the base part (9), which in combination with the boundary surface (19) forms the measuring cell (12) through which the sample, for example coming from the mixing region (6), is moved by means of positive or negative pressure, preferably with a constant, homogeneous flow rate. This measuring cell (12) is characterized here by a particularly low height compared with the other channels of an optionally upstream and/or downstream microfluidic structure. As a result, the sample volume is utilized to the optimum, since a longest possible measurement time at a highest possible flow rate is rendered possible. A preferred height of the measuring cell (12) is ≤300 μm.

At the boundary surface (19) in the measuring cell (12), at least one trapping zone (21) is provided, in which trapping molecules are arranged, which capture the molecules of interest from the sample liquid and fix them on the boundary surface so that the fluorescence can be excited and measured there are arranged.

For the measurement of the fluorescence, a detector (20) for measurement of a fluorescence intensity which changes with respect to time (e.g. PMT or CCD camera) is provided in a measuring device in which the measuring cassette of FIG. 5 is arranged.

In the embodiment of FIG. 5, the light entry area is a plane (18a). In the alternative embodiment of a measuring cassette according to the invention which is shown in FIG. 6, for the excitation radiation the light entry area is configured as a converging lens (18b). The converging lens (18b) ensures that in this embodiment the light beam from the light source (17) always meets the boundary surface (19) centrally within the region of the measuring cell (12) and the effects of variations in insertion on an evanescent field forming under total reflection are therefore compensated. This compensation reduces positioning-related variations in the evanescent field, i.e. the penetration depth or intensity thereof, compared with known systems.

FIG. 7 is diagram of an embodiment of a measuring device according to the invention. The beam path of the excitation light from the light source (17) and of the fluorescence light from the measuring cell to the detector (20), inter alia, are shown.

The light source (17) and the detector (20) are connected to one another mechanically in the measuring apparatus in one plane to form a unit. This unit and the measuring cassette of body (1) and base (9) for the measurement are moved relative to one another. In this context, the light source (17) is arranged transversely to the direction of movement, so that the light beam radiates on to the boundary surface (19) transversely to the direction of movement. With this configuration, it has been possible to avoid essential disadvantages of the known system, since (i) the path of said light beam through the optically transparent region (2) is minimized, (ii) always only a small section of the optically transparent region (2) is illuminated, (iii) the path of the excitation light through said optically transparent region (2) is always the same length over the entire detection region and (iv) a better local resolution is achieved.

The thickness of the optically transparent region (2) here is to be chosen independently of the number of trapping zones (21). A large number of analytes can therefore be determined with one measurement at the various trapping zones (21) using only one light source (17) and only one fluorescent dyestuff for all the analytes, the same conditions for excitation and detection can be created over the entire scanning region and the effect of the intrinsic autofluorescence of the plastics can be reduced significantly and the signal-noise ratio therefore improved significantly.

LIST OF REFERENCE SYMBOLS

1 Body
2 Optical region
3 Sample filling opening
4 Mixing region
5 Zone for dissolving the tracer
6 Second mixing region
7 Sample waste region
8a, 8b Channel ends
9 Base
11a, 11b Pressure connection openings
12 Measuring cell
13 Toothed structure
14 Recesses
15 Coupling of light
16 Detector
17 Light source
18 Light entry area
19 Boundary surface
20 Fluorescence detector
21 Trapping zone
22 Cover
23 Recess in Cover

The invention claimed is:

1. A replaceable disposable measuring cassette for introduction into a measuring device for detecting target molecules in a liquid sample by measurement of fluorescence emission, comprising:
a body of an optically transparent material having an upper-side, an under-side, and a surface providing a light entry area where excitation radiation provided by the measuring device enters into the body, wherein, when introduced into the measuring device, the upper side faces a top portion of the measuring device and the under-side faces a bottom portion of the measuring device;
a base directly contacting the under-side of the body;
a microfluidic structure formed by a combination of recesses in the body and in the base that contains a liquid sample that is moveable within the microfluidic structure, wherein the microfluidic structure comprises a flow-through measuring cell and at least one of the following arrangements a) to c): a) a zone for dissolving a tracer; b) a sample mixing region, or c) a liquid detection region, wherein the flow-through measuring cell is a recess within the microfluidic structure in which excitation radiation provided by the measuring device generates an evanescent field in the liquid sample on a base material side of a boundary surface of the liquid sample and the measuring cell;
areas on which the body and the base contact each other and surround the recess forming the microfluidic structure are bonded to one another directly and in a fluid-tight manner by laser welding; and
several different trapping zones provided in the measuring cell and configured to respond to several different analytes at the various trapping zones using only one light source,
wherein the surface of the body providing the light entry area forms a converging lens which always directs the beam of the excitation radiation centrally along the longitudinal axis of the measuring cell exactly to the desired point of the boundary surface of the liquid sample and the surface of the transparent material of the body at which the fluorescence emission to be measured is to be generated.

2. The measuring cassette according to claim 1, wherein the microfluidic structure further comprises at least two of the following arrangements a) to c):
a) a zone for dissolving a tracer,
b) a sample mixing region, or
c) a liquid detection region.

3. The measuring cassette according to claim 1, wherein at least one of the body or the base is an injection molded single component part.

4. The measuring cassette according to claim 1, further comprising an electronic memory chip which can be written to and overwritten through the packaging even after packing of the measuring cassette.

5. The measuring cassette according to claim 1, further comprising a sample filling opening in the body configured to introduce the sample into the measuring cassette, the sample filling opening being closable in a pressure-tight manner.

6. The measuring cassette according to claim 1, further comprising pressure openings passing through the base or the body and connected to the microfluidic structure, the pressure openings for connection with a pump to create positive or negative pressure to move the sample through the microfluidic structure.

7. The measuring cassette according to claim 1, wherein the microfluidic structure further comprises a sample waste region.

8. The measuring cassette according to claim 1, further comprising a cover joined to the body that at least partly covers the body, wherein the cover comprises a recess that exposes the body in the region of the recess, wherein the recess in the cover is at least in the region of the beam path of the excitation radiation and the fluorescence emission.

9. The measuring cassette according to claim 8, wherein the body, the base, and the cover are each an injection molded single component part.

10. The measuring cassette according to claim 8, wherein hot caulking connects the cover to the body.

11. The measuring cassette according to claim 1, wherein the tracer comprises a fluorescent marker.

12. The measuring cassette according to claim 1, wherein the sample mixing region comprises a snake mixer, in which the recesses of the microfluidic structure follow a serpentine path.

13. The measuring cassette according to claim 1, wherein the liquid detection region comprises a portion of the microfluidic structure in which a light beam is passed through and the refraction of that light beam is observed to determine if there is any air in the microfluidic structure.

14. A measuring system for the detection of target molecules in a liquid sample by measurement of fluorescence emission after excitation in an evanescent field, comprising:
  a measuring device; and
  a plurality of replaceable measuring cassettes, each replaceable measuring cassette comprising:
    a body of an optically transparent material having an upper-side, an under-side, and a surface providing a light entry area where excitation radiation provided by the measuring device enters into the body, wherein, when introduced into the measuring device, the upper side faces a top portion of the measuring device and the under-side faces a bottom portion of the measuring device;
    a base contacting the under-side of the body;
    a microfluidic structure formed by a combination of recesses in the body and in the base that contains a liquid sample that is moveable within the microfluidic structure, wherein the microfluidic structure comprises a flow-through measuring cell and at least one of the following arrangements a) to c): a) a zone for dissolving a tracer; b) a sample mixing region, or c) a liquid detection region, wherein the flow-through measuring cell is a recess within the microfluidic structure in which excitation radiation provided by the measuring device generates an evanescent field in the liquid sample on a base material side of a boundary surface of the liquid sample and the measuring cell;
    areas on which the body and the base contact each other and surround the recess forming the microfluidic structure are bonded to one another directly and in a fluid-tight manner by laser welding; and
    several different trapping zones provided in the measuring cell and configured to respond to several different analytes at the various trapping zones using only one light source,
  wherein the surface of the body providing the light entry area forms a converging lens which always directs the beam of the excitation radiation centrally along the longitudinal axis of the measuring cell exactly to the desired point of the boundary surface of the liquid sample and the surface of the transparent material of the body at which the fluorescence emission to be measured is to be generated,
  wherein the measuring device comprises:
    an insertion shaft configured to receive one of the plurality of replaceable measuring cassettes at a time; and
    a holder configured to provide a relative movement of the one of the plurality of replaceable measuring cassettes with respect to the light source for the excitation radiation, in order to bring various regions of the measuring cell into the beam path of the excitation radiation and to be able to respond to several different analytes in several different trapping zones provided in the measuring cell using only one light source;
    a light source that creates an excitation radiation, which is arranged in the measuring device such that the beam of the excitation radiation meets the measuring cell at an angle of 90 degrees to the direction of the relative movement of the measuring cassette with respect to the light source; and
    a detector arranged on the top portion of the measuring device and configured to detect the evanescent field.

15. The measuring system according to claim 14, wherein the measuring device further comprises a pressure source, wherein each replaceable measuring cassette further comprises pressure openings through the base or the body and connected to the microfluidic structure and the pressure source such that the positive or negative pressure generated by the pressure source moves the sample through the microfluidic structure.

16. A method for detecting target molecules in a liquid sample by measurement of fluorescence emission after excitation in an evanescent field, comprising using the system according to claim 14 by:
  inserting a liquid sample into the microfluidic structure of one of the plurality of replaceable measuring cassettes;
  inserting the one of the plurality of replaceable measuring cassettes into the measuring device;
  applying excitation radiation from the light source to the measuring cell; and
  detecting the evanescent field generated by the excitation radiation at the boundary surface of the surface of the transparent material of the body and the liquid sample in the measuring cell with the detector.

17. The method according to claim 16, wherein the liquid sample is a body fluid or an aqueous sample for foodstuffs or environmental analysis, wherein the sample is optionally treated or not treated for the detecting of the target molecules.

18. The measuring system according to claim 14, wherein the tracer comprises a fluorescent marker.

19. The measuring system according to claim 14, wherein the sample mixing region comprises a snake mixer, in which the recesses of the microfluidic structure follow a serpentine path.

20. The measuring system according to claim 14, wherein the liquid detection region comprises a portion of the microfluidic structure in which a light beam is passed through and the refraction of that light beam is observed to determine if there is any air in the microfluidic structure.

* * * * *